United States Patent [19]

Angelchik

[11] Patent Number: 4,648,383
[45] Date of Patent: Mar. 10, 1987

[54] PERORAL APPARATUS FOR MORBID OBESITY TREATMENT

[76] Inventor: Jean P. Angelchik, 1728 W. Glendale Ave., Phoenix, Ariz. 85021

[21] Appl. No.: 757,158

[22] Filed: Jul. 22, 1985

Related U.S. Application Data

[60] Continuation-in-part of Ser. No. 690,852, Jan. 11, 1985, Pat. No. 4,607,618, which is a division of Ser. No. 469,095, Feb. 23, 1983, abandoned.

[51] Int. Cl.$^4$ .............................................. A61B 17/00
[52] U.S. Cl. ................................. 128/1 R; 128/303 R
[58] Field of Search ............... 128/344, 303 R, 348.1, 128/345, 1 R; 604/96

[56] References Cited

U.S. PATENT DOCUMENTS

| | | | |
|---|---|---|---|
| 4,416,267 | 11/1983 | Garren et al. | 128/344 X |
| 4,425,908 | 1/1984 | Simon | 128/303 R X |
| 4,580,568 | 4/1986 | Gianturco | 604/96 X |

Primary Examiner—Michael H. Thaler
Attorney, Agent, or Firm—William H. Drummond

[57] ABSTRACT

Apparatus for peroral treatment of morbid obesity includes a collapsible intra-gastric appliance which can be temporarily deformed to pass through the esophagus and cardiac opening of the stomach and to autogenously assume a normal shape after it is received in the stomach to stimulate neuro-receptors in the sub-mucosa of the gastric fundus. Means are provided for detachably connecting the appliance to the lower end of an elongate, semi-rigid inserter rod which is passed through an aperture formed in the appliance to effect the detachable connection. Downward pressure on the inserter rod forces the collapsed appliance through the esophagus and cardiac opening into the stomach and slight upward force of the inserter rod is thereafter applied to detach the rod from the appliance.

1 Claim, 5 Drawing Figures

PERORAL APPARATUS FOR MORBID OBESITY TREATMENT

More particularly, this application is a continuation in part of my co-pending application, Ser. No. 690,852 filed Jan. 11, 1985 U.S. Pat. No. 4,607,618 entitled "Method for Treatment of Morbid Obesity", which is a division of Ser. No. 469,095 filed Feb. 23, 1983, abandoned.

This invention relates to apparatus for peroral treatment of morbid obesity without surgery.

In still another aspect, the invention concerns such improved apparatus in which a collapsible intra-gastric appliance is emplaced in the gastric fundus with improved convenience and reduced discomfort for the patient.

In still another aspect the invention relates to peroral emplaceable applicances for treatment of morbid obesity which may have biodegradable parts which dissolve under normal stomach conditions after a preselected time to permit the remains of the appliance to be passed from the body through the intestines, such that removal of the appliance by surgery is unnecessary.

In my co-pending application, identified above, I describe a method for treatment of morbid obesity which generally includes the step of implanting within the gastric fundus a collapsible appliance which can be temporarily deformed by external force to permit peroral emplacement of the appliance through the esophagus and cardiac opening of the stomach, after which the appliance autogenously assumes its normal shape and is received and retained in the gastric fundus.

When so-emplaced, the appliance functions to cause distention of the stomach and concomitent excitation of neuroreceptors in the sub-mucosa of the upper fundus. Excitation of these neuroreceptors, which are endings of the vegus nerves of the gastric plexus, causes the patient to experience the sensation of satiety, even though the patient has ingested only a relatively small amount of food.

As originally conceived, the appliance disclosed in my co-pending application was adapted for insertion through the esophagus and cardiac opening of the stomach through a cylindrical bougie. The appliance was temporarily collapsed to permit insertion within the bougie and then the bougie containing the collapsed appliance was inserted through the esophagus and cardiac opening. The collapsed appliance was ejected from the lower end of the bougie into the stomach by means of a piston-like device operating in the bougie above the collapsed appliance.

While the method of insertion described in my copending application and summarized above is feasible, it would be highly desirable to provide apparatus for the treatment of morbid obesity which permits emplacement of the appliance with less discomfort to the patient and greater convenience to the clinician.

Accordingly, it is the principal object of the present invention to provide apparatus for the treatment of morbid obesity which permits rapid, convenient and less painful emplacement of an intra-gastric appliance.

Yet another object of the invention is to provide apparatus for treatment of morbid obesity which, because of its simplicity of use, is especially adapted to treatments which involve periodic and recurring removal and replacement of the intra-gastric appliance.

These and other, further and more specific objects and advantages of the invention will be apparent to those skilled in the art from the following detailed description thereof, taken in conjunction with the drawings in which.

Briefly, in accordance with my present invention, I provide apparatus for peroral treatment of morbid obesity which comprises a collapsible intra-gastric appliance dimensioned and normally shaped to be received and retained within the gastric fundus, which is temporarily deformable by external force to a collapsed shape which is cross-sectionally dimensioned to be inserted through the esophagus and cardiac opening of the stomach and which is adapted to autogenously assume its normal shape after the appliance is received in the stomach, such appliance also including means for detachable connection to the lower end of an elongate semi-rigid inserter rod and means defining an aperture in such appliance, through which said rod can be inserted to effect such detachable connection.

Figure 1:
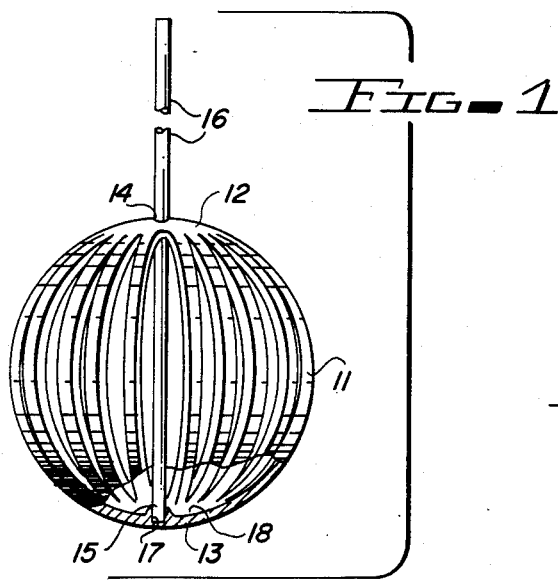
FIG. 1 is a partially cut-away view of an intragastric appliance which is configured for use in accordance with the present invention, showing the appliance in the normal, uncollapsed shape.

Turning now to the drawings, in which like reference characters identify the same elements in the several views, the appliance, shown in FIG. 1 in its normal shape, can be constructed in any desired fashion to render it temporarily collapsible, for example, as shown in FIG. 1 by forming it in a generally spherical configuration from a plurality of semi-rigid skeleton members 11 joined at their upper and lower ends 12 and An aperture 14 is provided in the upper portion 12 of the appliance, through which can be passed the lower end 15 of an inserter rod 16.

Figure 3:
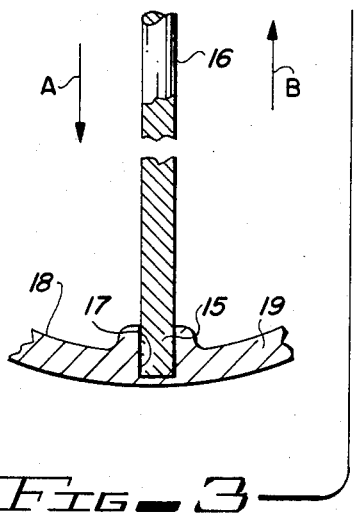
FIG. 3 is a sectional view of the lower portions of the appliance and inserter rod of FIG. 2, showing the presently preferred mode of effecting the detachable connection of the inserter rod to the intra-gastric appliance.

Referring to FIG. 3, the lower end 15 of the inserter rod is received and frictionally engaged in a socket 17 formed in the inner wall 18 of the lower portion of the appliance wall 19.

The rod 16 is detachably connected to the appliance 19 by applying downward pressure in the direction of the arrow A on the rod 16 to force the end 15 into frictional engagement in the socket 17, effecting a detachable connection between the rod 16 and the appliance.

Figure 2:
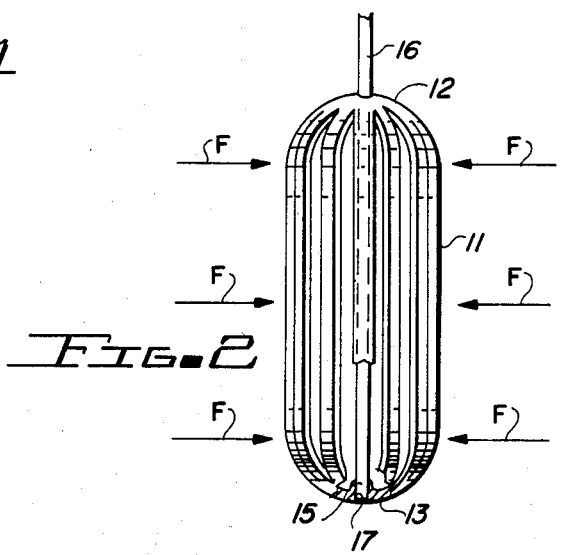
FIG. 2 is a partially cut-away view of the appliance of FIG. 1 in the temporary collapsed shape with an inserter rod attached prior to emplacement of the appliance in the gastric fundus.

As will be seen, the appliance of FIGS. 1-2 is thus temporarily and detachably connected to the rod 16 in such fashion that considerable downward force in the direction of the arrow A can be exerted. However, relatively little force in the direction of the arrow B is required to overcome the frictional engagement of the rod 16 in the socket 17, allowing the rod 16 to be withdrawn from the appliance through the aperture 14.

Figure 4A:
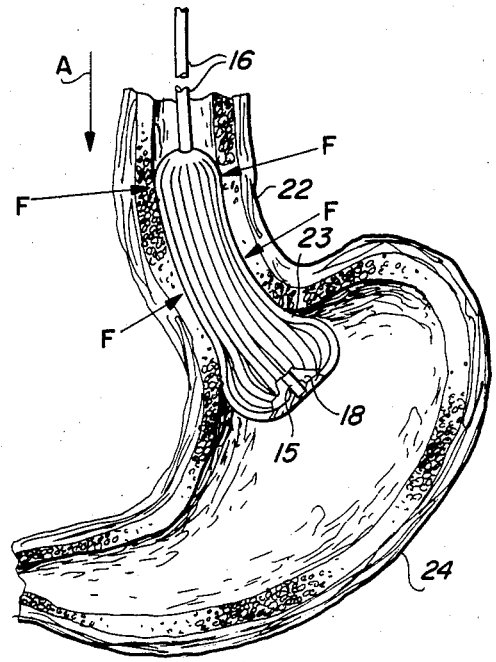
FIG. 4A is a sectional view of the distal esophagus and stomach with the appliance of FIGS. 1 and 2 partially inserted within the stomach.
Figure 4B:
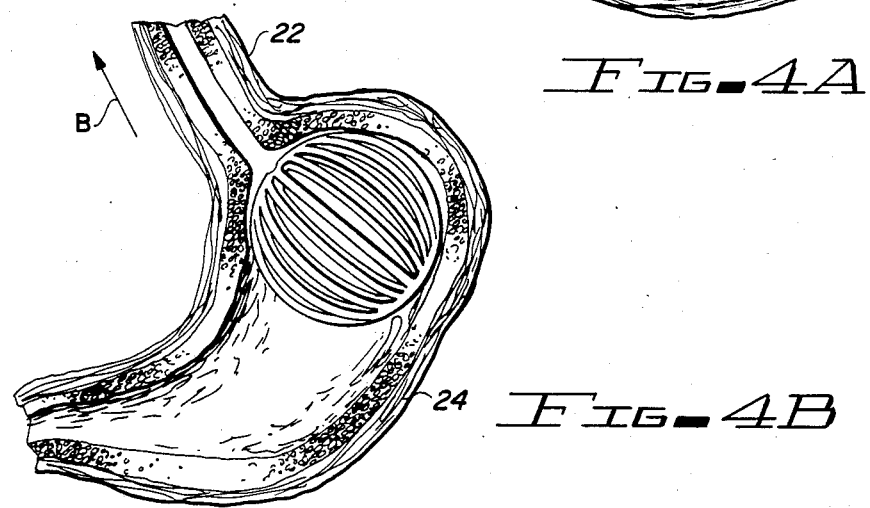
FIG. 4B is a sectional view like FIG. 4A except that the appliance of FIGS. 1-2 is shown after it is completely received in the gastric fundus and just prior to detachment of the inserter rod.

As shown in FIGS. 4A and 4B, the collapsed appliance of FIG. 2 and attached rod 16 is inserted through the esophagus 22 by applying downward force in the direction of the arrow A on the rod 16. The inwardly directed force F exerted by the inner walls of the esophagus 22 maintains the appliance in the collapsed condition of FIG. 2 until it emerges (as partially shown) from the cardiac opening 23 of the stomach 24.

As shown in FIG. 4B, once the entire appliance of FIGS. 1–2 is received in the gastric fundus, it autogenously assumes its normal, generally cylindrical shape, after which the inserter rod 16 can be removed by applying a relatively small force in the direction of the arrow B to effect the disconnection of the lower end 15 of the rod 16 from the socket 17 in the lower end of the appliance.

In accordance with a presently preferred, but alternate embodiment of the invention, the appliance or portions thereof of FIGS. 1–2 can be fabricated from materials which biodegrade in the stomach after preselected periods of time. By appropriate selection of the biodegradation time, the appliance of FIGS. 1–2 can be caused to be ejected from the stomach by normal processes at such time as it has achieved the desired physiological result.

Alternatively, if desired, a treatment regimen can be adopted in which a plurality of the appliances are successively implanted, the new device being implanted after the previous device has been biologically degraded to permit its passage through the intestinal tract. In this fashion, a single appliance can be removed from the stomach without surgery prior to the time it becomes encrusted and replaced with a new, clean appliance.

According to a further embodiment of the invention, either the appliance or the inserter rod, or preferably both, can be formed or partially formed of radio-opaque material to permit visual observation of the apparatus during and after emplacement by fluroscopic or X-ray techniques.

Having described my present invention in such terms as to enable those skilled in the art to understand and practice it and, having identified the presently preferred embodiments thereof,

I claim:

1. Apparatus for peroral treatment of morbid obesity comprising a collapsible intra-gastric appliance, said appliance being a collapsible, hollow, shaped device which is normally shaped and dimensioned to be received and retained within the fundus without deforming the stomach walls beyond its normal shape and dimensions, formed of a semi-rigid skeleton which is collapsible by the application of external force to deform said device to a shape and cross-sectional dimension which is insertable into the stomach through the esophagus and the cardiac opening, and capable of autogenously reassuming and retaining said normal shape when such collapsing external force is removed, said appliance also including
  (a) means for detachable connection to the lower end of an elongate semi-rigid inserter rod, and
  (b) means defining an aperture in said appliance through which said rod can be passed to effect such detachable connection.

* * * * *